US00PP08912P

United States Patent [19]

Zaiger et al.

[11] Patent Number: Plant 8,912

[45] Date of Patent: Sep. 27, 1994

[54] INTERSPECIFIC ROOTSTOCK "VIKING"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 100,284

[22] Filed: Aug. 2, 1993

[51] Int. Cl.[5] ..... A01H 5/00

[52] U.S. Cl. ..... Plt./42.1

[58] Field of Search ..... Plt. 42.1

[56] References Cited

PUBLICATIONS

Kester et al. 1975 *In* Advances in Plant Breeding (eds. Janick et al.) Purdue Univ. Press; pp. 412–419.

Kester et al. 1987 *In* Rootstocks for fruit crops (eds Rom et al.) John Wiley & Sons; pp. 265–293.

*Primary Examiner*—Patricia R. Moody

[57] ABSTRACT

A new and distinct interspecific rootstock tree having the following unique combination of outstanding features that are desirable in a new rootstock variety:

1. The ability to develop roots from dormant cuttings when planted in the field.
2. Produces little to no root suckers.
3. Rapid rooting and growth of the cuttings in the field, facilitates early spring budding of peaches and almonds.
4. Vigorous upright growth.
5. Well anchored, deep root system.
6. Has scion compatibility with Almonds (*Prunus amygdalus*) and Peaches (*Prunus persica*)

1 Drawing Sheet

ORIGIN OF THE VARIETY

The new and distinct variety of interspecific rootstock tree was originated by us in our experimental orchard located near Modesto, Calif. as a first generation seedling of a cross between Nemaguard Rootstock (non-patented) and a selected seedling with the identification number 14H528. The selected seedling 14H528 originated from a cross between *Prunus amygdalus* cv. Jordanolo (non-patented) and *prunus blireiana. Prunus blireiana* parentage being *Prunus cerasifera* cv. "Atropurpures"×Prunus Mume apricot. This first generation cross gave the genetic background to our new interspecific rootstock selection as being ½ peach, ¼ almond, ⅛ plum and ⅛ apricot. A large group of first generation seedlings were grown and maintained under close observation by us, one seedling which is the present rootstock variety showed extra vigor, upright growth, large leaves with a very thrifty appearance was selected for asexual propagation by cuttings and budding.

ASEXUAL REPRODUCTION OF THE VARIETY

The present new variety of interspecific rootstock tree was asexually propagated by cuttings and budding, as performed by us in our experimental orchard located near Modesto, Calif. and shows that all characteristics are estblished and run true to the original tree in all respects.

SUMMARY OF THE VARIETY

The herein new and distinct variety of interspecific rootstock tree which is of laarge size, medium dense, upright in growth and the cuttings from this tree have the ability to develop roots when planted directly into the field. The present variety of rootstock tree is further characterized by the rapid rooting of its cuttings allowing for early spring budding of peaches or almonds, producing few if any root or trunk suckers, and being well anchored with a deep root system. In comparison with the Nemaguard rootstock which is propagated from seed, the new interspecific rootstock Viking, which is grown from cuttings, can be budded earlier to peaches and almonds in the spring producing larger, more uniform trees by digging time in the late fall. The trees planted of Butte almond (U.S. Plant Pat. No. 2,380) and Padre almond (non patent) on Nemaguard rootstock compared to the Butte and Padre almond trees planted on Viking rootstock show that the trees on Viking rootstock are more uniform, approximately 25% larger in size, having greater production and bearing almonds with larger kernel size. In comparison to peaches budded to Nemaguard and Viking rootstocks, cvs. Corona, Andross (non-patented) Stanislaus (U.S. Plant Pat. No. 8,376), the new peach selections 28K217, 58GC112, 163GE300, 168GE118, 26K6, 32K95, 5GD5 and the interspecific tree Tri-lite (U.S. Plant Pat. No. 8,393), the trees budded to Viking Rootstock are approximately 25% larger in size, have a greater number of fruit set in the second and third year of growth, the fruit being larger and more uniform in size at thinning time and at maturity having greater production of large size fruit.

In comparison to the Almond cv. Padre budded to the rootstocks Hansen 536, Hansen 2168 and the rootstock Viking and planted on irrigated clay loam soil, the Viking rootstock has a greater tolerance to heavy wet soils and is less susceptible to Phytophthora species.

Trees budded to clonally grown rootstocks such as Viking are more uniform in size than rootstocks grown from seed such as Bright's Hybrid or Titan Hybrid. In comparison to the French Hybrid rootstock GF677, the Viking rootstock has greater rooting ability and the cuttings can be rooted in the field, budded and developed into desirable trees in one year instead of two years as needed for the rootstock GF677.

BRIEF DESCRIPTION OF THE PHOTOGRAPHS

The accompanying photographic illustrations show typical specimens of the fruit and foliage of our new interspecific rootstock variety. The upper and lower surface of the leaves illustrated, the exterior of the fruit and a fruit divided on its suture plane to reveal flesh, pit cavity and a stone remaining in place. The photographs were taken shortly after being picked (soft ripe) and the colors are as nearly true as is reasonably possible in a color representation of this type.

DESCRIPTION OF THE VARIETY

The following is a botanical description of the new and distinct variety of interspecific rootstock tree, its flowers, foliage and fruit as based on observations of the specimens grown near Modesto, Calif., with color terminology (except those in common terms) in accordance with Reinhold color Atlas by A. Kornerup and J. H. Wanscher.

Tree:
- *Size.*—Large.
- *Vigor.*—Vigorous.
- *Density.*—Medium dense.
- *Form.*—Upright.
- *Production.*—Productive.

Trunk:
- *Size.*—Large — stocky.
- *Texture.*—Shaggy.

Branches:
- *Size.*—Large.
- *Surface.*—Smooth to medium rough.
- *Lenticels.*—Medium to large size. Numerous.
- *Color.*—Light brown to brown — (5-D-5) to (5-E-4).

Leaves:
- *Size.*—Large. Average length — $6\frac{1}{2}''$. Average width — $1\frac{3}{4}''$.
- *Form.*—Lanceolate. Pointed.
- *Thickness.*—Medium.
- *Texture.*—Medium.
- *Margin.*—Crenate.
- *Petiole.*—Average length — $\frac{1}{2}''$. Average thickness — 3/32".
- *Glands.*—Number varies from 2 to 5. Average number 3. Located on upper portion of petiole and on base of leaf blade. Reniform.
- *Color.*—Upper surface — green to dark green — (28-F-5) to (28-F-8). Lower surface — light green — (28-E-6) to (28-E-8).

Flower Buds:
- *Size.*—Medium.
- *Length.*—Medium.

Flowers:
- *Blooming period.*—Mar. 1, 1992 to Mar. 8, 1992. Varies slightly with climatic conditions.
- *Size.*—Medium, non-showy.
- *Pollen.*—Present.
- *Color.*—Light pink.

Fruit:
- *Maturity when description.*—Soft ripe.
- *Date of maturity.*—Aug. 20, 1992 to Aug. 25, 1992.
- *Size.*—Small. Average diameter axially — 2". Average transversely in suture plane — $1\frac{3}{4}''$.
- *Form.*—Globose slightly elongated in suture plane.
- *Surface.*—Irregular, slight depressions and ridges throughout, no set pattern.
- *Ventral surface.*—Usually recessed, varies from shallow to pronounced.
- *Suture.*—Usually pronounced from stem to apex, slightly deeper at stem end.
- *Cavity.*—Rounded with irregular surface, usually slightly elongated in suture plane.
- *Apex.*—Usually a slight pistol point, varies from rounded to pointed.

Skin:
- *Thickness.*—Medium.
- *Tendency to Crack.*—None.
- *Down.*—Moderate to heavy.
- *Tenacity.*—Tenacious to flesh.
- *Color.*—White to yellowish white — (3-A-1) to (3-A-2).

Flesh:
- *Flavor.*—Very poor — non-eatable.
- *Juice.*—poor — lacking.
- *Fiber.*—Moderate to heavy.
- *Texture.*—Soft to very soft.
- *Ripen.*—Fairly even.
- *Eating quality.*—Very poor — value.
- *Color.*—White to pearl white — (2-A-1).

Stone:
- *Type.*—Semi-freestone. Adheres slightly to flesh fibers.
- *Size.*—Medium to large. Average length —$1\frac{1}{8}''$. Average breadth —1". Average thickness — $\frac{5}{8}''$.
- *Form.*—Ovoid.
- *Base.*—Usually straight, varies from straight to slightly rounded.
- *Apex.*—Cuspidate.
- *Sides.*—Nearly equal.
- *Surface.*—Irregularly furrowed toward apex and slightly pitted toward base.
- *Tendency to crack.*—None.
- *Color.*—Brown to reddish brown — (9-D-5) to (9-D-8).

Use: No Commercial value for the fruit. Clonal Rootstock propagated by dormant cuttings.

The tree, its flowers, foliage and fruit herein described may vary in slight detail due to climatic, soil and cultural practices under which the tree maybe grown; the present description being that of the variety grown under the ecological conditions prevailing near Modesto, Calif.

The following is claimed:

1. A new and distinct interspecific rootstock tree substantially as illustrated and described which is of large size, vigorous upright in growth (the variety being particularly characterized by its ability to reproduce by cuttings planted directly in the field), is well anchored with a deep root system, produces little to no root suckers, is compatible with almonds and peaches; in comparison to trees budded to Nemaguard rootstock the scion tree is approximately 25% larger in size, having greater production of fruit and nuts.

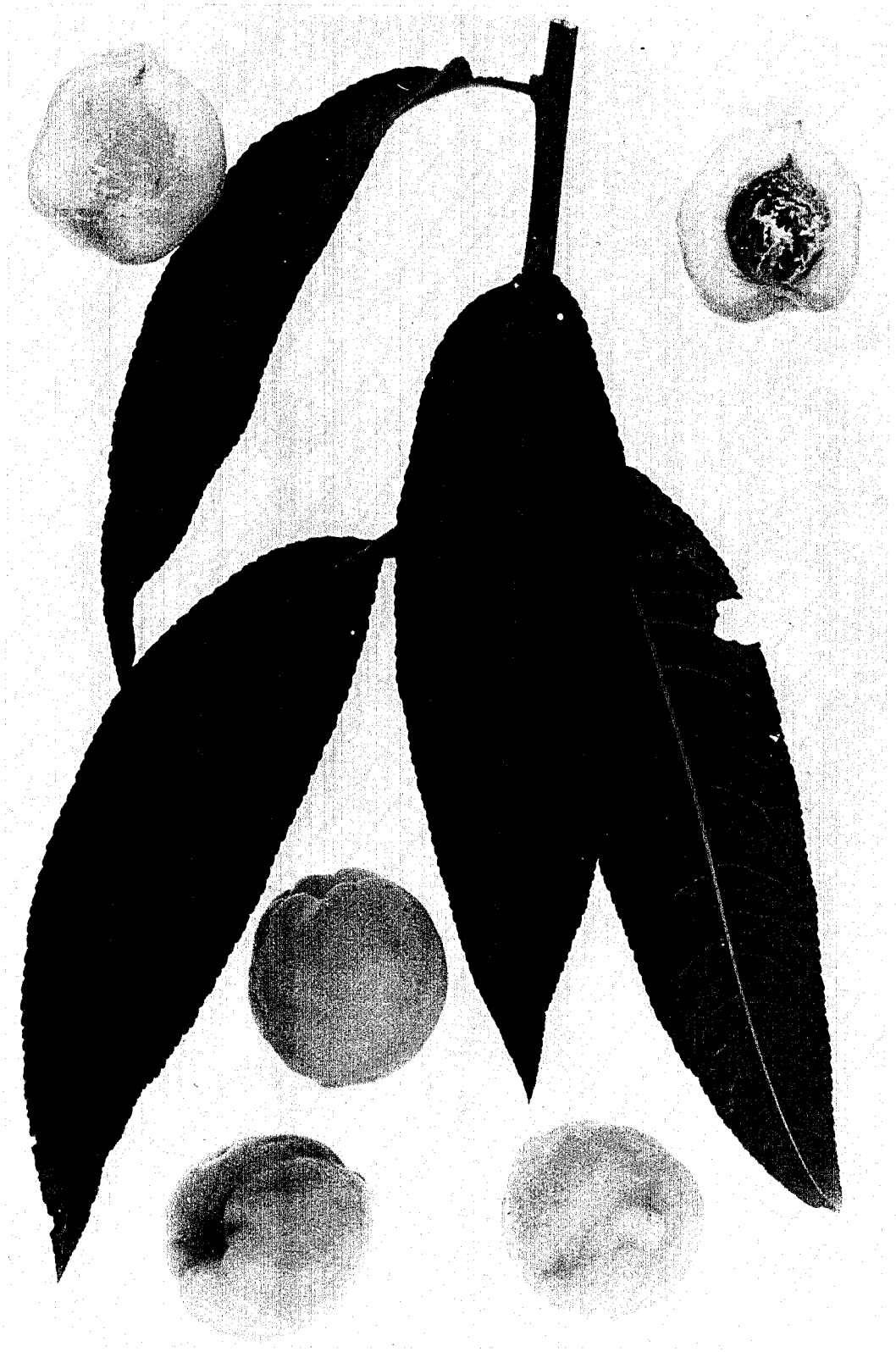

* * * * *